United States Patent [19]

Baier

[11] Patent Number: 5,098,375
[45] Date of Patent: Mar. 24, 1992

[54] UNIT FOR INSUFFLATING AND CLEANING GAS

[75] Inventor: Manfred Baier, Knittlingen, Fed. Rep. of Germany

[73] Assignee: Richard Wolf GmbH, Knittlingen, Fed. Rep. of Germany

[21] Appl. No.: 529,976

[22] Filed: May 29, 1990

[30] Foreign Application Priority Data

Jul. 11, 1989 [DE] Fed. Rep. of Germany ....... 3922746

[51] Int. Cl.⁵ .............................................. A61M 37/00
[52] U.S. Cl. ......................................... 604/23; 604/26; 128/747
[58] Field of Search ............... 604/21, 23–26, 604/27, 28, 30, 35; 128/747; 606/2, 10–12

[56] References Cited

U.S. PATENT DOCUMENTS

| | | | |
|---|---|---|---|
| 4,538,594 | 9/1985 | Boebel et al. | 128/6 |
| 4,735,603 | 4/1988 | Goodson et al. | 604/26 |
| 4,895,144 | 1/1990 | Cook et al. | 604/30 |
| 4,966,578 | 10/1990 | Baier et al. | 604/26 |
| 4,971,034 | 11/1990 | Doi et al. | 128/747 |
| 5,013,294 | 5/1991 | Baier | 604/26 |

*Primary Examiner*—Stephen C. Pellegrino
*Assistant Examiner*—Ralph A. Lewis
*Attorney, Agent, or Firm*—Panitch Schwarze Jacobs & Nadel

[57] ABSTRACT

A insufflation unit for distending a body cavity such as a uterus which is to be examined or treated endoscopically has a gas control circuit which connects a gas supply unit to the endoscope via a flowmeter, a shut-off valve and a filter. Associated with this gas control circuit is an extractor circuit which comprises a pump whose suction end is coupled up to the output of the flowmeter. A pressure-measuring transducer logs the pressure at the suction end of the pump and its measurements, together with those from the flowmeter, are made use of in analyzer electronics by switching off the pump before a pressure likely to put the patient at risk occurs should there be a fault in the extractor circuit.

2 Claims, 1 Drawing Sheet

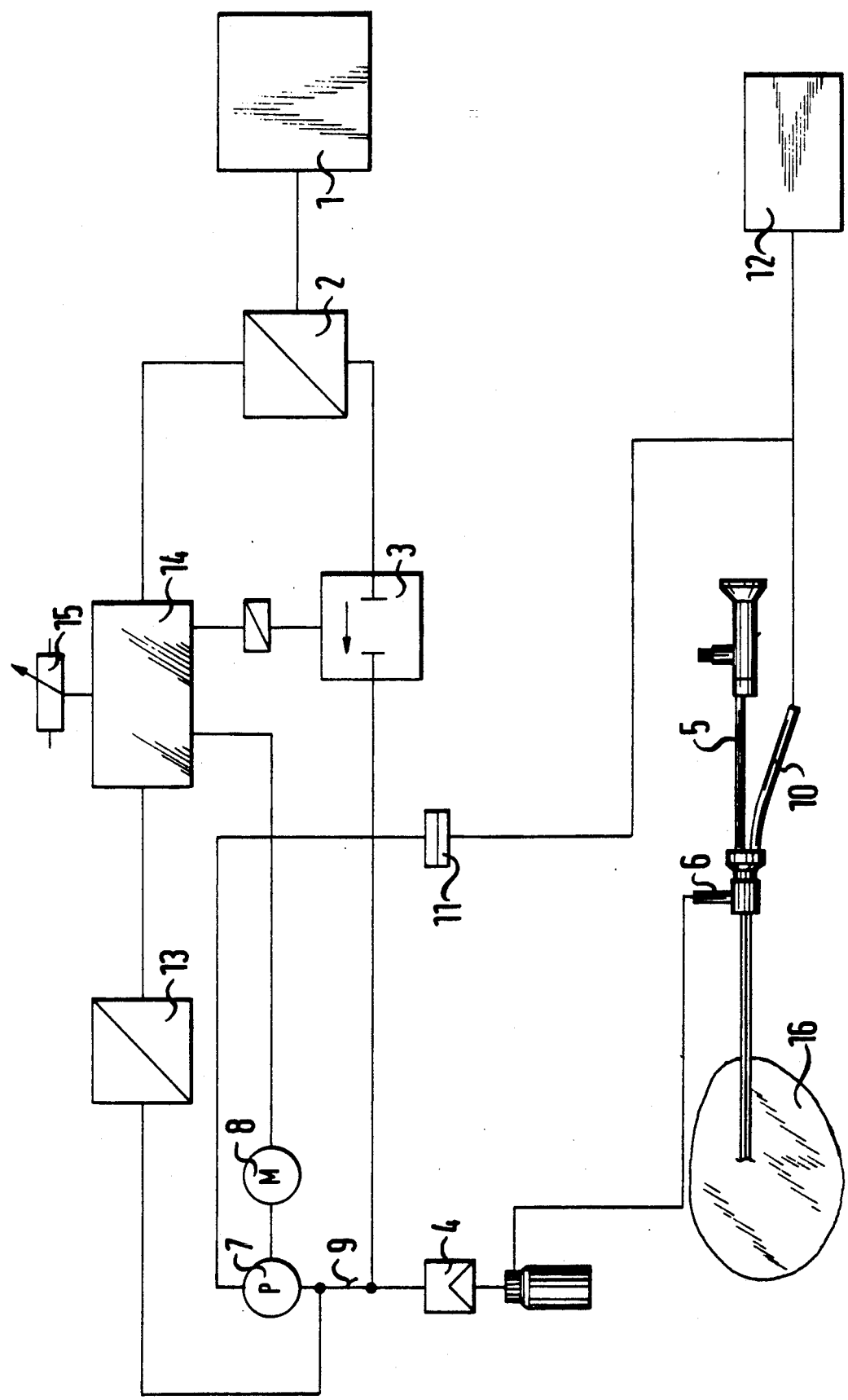

UNIT FOR INSUFFLATING AND CLEANING GAS

BACKGROUND OF THE INVENTION (a) Field of the Invention

This invention relates to an insufflation unit for use in endoscopic operations and in particular in human medicine, in which a gas which is introducible into a body cavity such as the uterus from a gas supply device via an instrument channel in the endoscope is monitored for pressure and flow rate and can be fed through a filter-equipped extractor circuit to filter out smoke and/or vapor.

(b) Description of the Prior Art

Units of this kind are needed to distend in the requisite manner a body cavity which is to be examined and treated in the course of an endoscopic operation. At the same time it is necessary that the pressure inside the body cavity should be kept as constant as possible during the operation.

It is known from DE-OS-3739003 (U.S. Pat. No. 5,013,294) to provide an insufflation unit with two flow paths and which is able constantly to compensate for minor losses of gas. Larger losses of gas, which may be be caused by a change of instruments or the like, can quickly be compensated for by changing over to the second flow path before the preselected lower pressure limit is reached. It is also ensured that, should the preselected upper pressure limit be overrun, the supply line and pump and any other ancillary devices which are connected to the outlets and operated by the analyser electronics are switched off and no more gas is fed into the body cavity.

DE-PS 3329784 (U.S. Pat. No. 4,538,594) discloses another unit of this kind which is suitable for use with coagulating instruments such as lasers. In this case there is a requirement that the smoke produced during the coagulation should be withdrawn as quickly as possible because it hampers the visual monitoring of the operation, and the withdrawal process must be carried out without the pressure in the body cavity changing. In the present prior art device this is done by extracting the smoke together with secretion and insufflation gas, the gas being cleaned by a filter and fed back into the body cavity in closed circuit.

Known insufflation units which have high gas flow-rates to produce the desired fast correction of pressure are not suitable for endoscopy in small body cavities like the uterus because in this case it is important for the maximum infeed of gas which is acceptable under the given physiological conditions not to be exceeded.

The main object of the present invention is to overcome the disadvantage that the said insufflation units are not suitable for operations of the kind mentioned hereinabove.

SUMMARY OF THE INVENTION

To this end, the present invention consists in an insufflation unit for use in endoscopic operations and in particular in human medicine, in which a gas which is introducible into a body cavity such as the uterus from a gas supply device via an instrument channel in the endoscope is monitored for pressure and flow rate and can be fed through a filter-equipped extractor circuit to filter out smoke and/or vapor characterised in that, on its way to the instrument channel, the gas flows through a flowmeter, a shut-off valve and a filter, in that the extractor circuit comprises a pump whose suction end is connected between the filter and shut-off valve and which is connected to a further instrument channel via a sterile filter, and in that the monitoring is performed by analyser electronics which obtain their control data from a pressure-measuring transducer connected to the suction end of the pump and from the said flowmeter and which control the shut-off valve and the pump by comparing the actual value for pressure with a preset desired value.

The advantages achievable by means of the present invention lie in particular in the fact that, as well as being able to provide the required distension of the body cavity and hold the pressure constant in the bubble of gas so produced, the unit can also detect faults in the extractor circuit and react to them so that pressures which put the patient at risk cannot arise. What is more, units constructed according to the invention are also capable of preventing an insufflation if the gas throughput of the unit connected up for an operation is unsuitable, i.e. if a unit whose possible flow-rates are rather high is connected up.

BRIEF DESCRIPTION OF THE DRAWING

In order that the invention may be more readily understood an embodiment thereof will now be described, by way of example, with reference to the accompanying drawing which is a block circuit diagram of a unit which operates in accordance with the invention.

DESCRIPTION OF THE PREFERRED EMBODIMENT

Referring to the drawing, the block circuit diagram includes a gas control circuit which, via a flowmeter 2, a shut-off valve 3, a filter 4 and a connecting nozzle 6, connects an appropriate gas supply unit 1 to an instrument channel, connected to the connecting nozzle, in an endoscope 5. The block circuit diagram further includes an extractor circuit having a pump 7 driven by a motor 8 whose suction end 9 is connected to the outlet of the shut-off valve 3 and to the filter 4 and which is coupled up via a sterile filter 11 to an instrument channel 10 in the endoscope 5, being so coupled via the outer shell of the light guide of a laser unit 12, which outer shell surrounds the light guide at a distance. The pressure at the suction end 9 of the pump 7 is logged by a pressure-measuring transducer 13 which, like the flowmeter 2, transmits its measurement data to analyser electronics 14 which compare the measurements with the value preset from a setting device 15, the outputs of the analyser electronics 14 being connected to the shut-off valve 3 and the motor 8 of the pump 7.

The flowmeter 2 monitors flow to a limiting value and controls the shut-off valve 3 via the analyser electronics 14. For this purpose a desired/actual comparison is carried out in the analyser electronics 14 and the shut-off valve 3 is closed if the permitted flow-rate is exceeded. To distend a body cavity a flow of gas takes place through the shut-off valve 3. With the pump still off, this gas passes through filter 4 and into body cavity 16, such as a uterus. If a leak occurs in the gas circuit as the process is getting under way then, due to the low output capacity of the unit, the pressure does not rise to the preset level and the pump cannot be switched on. When the pressure preselected with the setting device 15 is reached, shut-off valve 3 is actuated and hence the flow of gas from the gas supply unit 1 is stopped. If use is then made of the laser unit 12, pump 7 can be switched on to extract the smoke produced. The pump cannot, though, be switched on if the preselected pressure has not been reached.

In this way the smoke is sucked out of the body cavity 16 with the gas and filtered out in filter 4 and the cleaned gas is then pumped back into body cavity 16 via the sterile filter 11 which is fitted to prevent the transmission of bacteria. The desired value preset for pressure should be between 40 mbar and 200 mbar. If the pressure drops below the preselected level by approximately 20 mbar, the circulation of the gas stops until the gas supply unit 1 has restored the pressure to the preset level. The pressure is measured by the pressure-measuring transducer 13 at the suction end 9 of pump 7, because at this point downstream of filter 4 and the large flow cross-section in the endoscope 5, given the filter throughout aimed at of 500 to 1000 ml/min, there is no substantial difference from the pressure in the body cavity. This ensures that there is a closed gas-circuit because if there are any losses of gas in the circuit, the change from the pre-selected level is sensed by the pressure-measuring transducer 13. If pressure were measured on the delivery side of pump 7, the ducts, which are generally small in cross-section (light guide outer shell) would cause an incorrect pressure reading. Leaks in the connecting lines or the endoscope 5 cause a drop in pressure in the extraction circuit which is detected by the analyser electronics 14 and causes the pump 7 to be switched off. Blockage of a rigid line or linking of a flexible one causes the pressure to drop below the set level and is detected as a fault in the circuit. If there is no gas supply, the intake of air is ruled out because the pump is then off.

The flowmeter 2, analyser electronics 14 and shut-off valve 3 may also be so designed that if a CO$_2$ supply unit with a higher flow-rate is going to be used, the flow-rate can be held down to the maximum rate permissible for the application. If endoscope 5 has enough connections, there is no need for the outer shell of the light guide to be brought into play to feed the gas into the gas circuit. The circuit can then be set up through other connections and the light guide can be inserted into a separate instrument channel through a suitable adapter.

Whilst a particular embodiment of the invention has been described it should be appreciated that variations and modifications may be made without departing from the scope of the invention.

I claim:

1. An insufflation unit for insufflating a small body cavity with a gas and for recycling said gas removed from said small body cavity, comprising:
   a gas supply unit for supplying a gas;
   a shut-off valve being in fluid communication with said gas supply unit having a first position such that gas flowing from said gas supply unit flows through said shut-off valve and a second position such that gas flowing from said gas supply unit is prevented from flowing through said shut-off valve;
   a filter being in fluid communication with said shut-off valve such that gas is able to flow from said shut-off valve through said filter, and for being in fluid communication with a first instrument channel of an endoscope which is in fluid communication with a body cavity such that fluid can flow between said body cavity and said filter through said first instrument channel;
   a pump having a suction end, said suction end being in fluid communication with said filter for withdrawing said gas within said body cavity through said first instrument channel and said filter, said pump having a delivery side for expelling said withdrawn gas;
   a sterile filter being in fluid communication with said delivery side of said pump for receiving and filtering said withdrawn gas and for being in fluid communication with a second instrument channel of said endoscope which is in fluid communication with said body cavity such that said filtered gas flows into said body cavity through said second instrument channel;
   a pressure sensor being in fluid communication with said suction end of said pump for sensing a pressure of said gas at said suction end of said pump which corresponds to a pressure of said gas within said small body cavity;
   control means for moving said shut-off valve between said first and second positions and for preventing said pump from being actuated in response to said sensed pressure, said control means comparing said sensed pressure to a predetermined pressure, said control means positioning said shut-off valve in said first position and preventing said pump from being actuated when said sensed pressure is less than said predetermined pressure for insufflating said small body cavity and said control means positioning said shut-off valve in said second position and permitting actuation of said pump when said sensed pressure is greater than or equal to said predetermined pressure for recycling said gas within said small body cavity.

2. An insufflation unit according to claim 1, further comprising a flowmeter being in fluid communication with said gas supply unit and said shut-off valve such that said gas flows from said gas supply unit through said flowmeter to said shut-off valve, said flowmeter for monitoring a volume of the gas flowing therethrough, said control means moving said shut-off valve between said first and second positions in response to said volume of gas flowing through said flowmeter, said control means further comparing said volume of gas flowing through said flowmeter to a predetermined volume, said control means positioning said shut-off valve in said first position when said volume is less than said predetermined volume for insufflating said small body cavity and said control means positioning said shut-off valve in said second position when said volume is greater than or equal to said predetermined volume for preventing said supplied gas from entering said small body cavity.

* * * * *